(12) United States Patent
Hoftman et al.

(10) Patent No.: US 9,687,621 B2
(45) Date of Patent: Jun. 27, 2017

(54) DUAL LUMEN ENDOBRONCHIAL TUBE DEVICE

(71) Applicants: Nir Hoftman, Los Angeles, CA (US); Aman Mahajan, Sherman Oaks, CA (US); Mike Hoftman, Chatsworth, CA (US)

(72) Inventors: Nir Hoftman, Los Angeles, CA (US); Aman Mahajan, Sherman Oaks, CA (US); Mike Hoftman, Chatsworth, CA (US)

(73) Assignee: The Regents of the University of California, Oakland, CA (US)

( * ) Notice: Subject to any disclaimer, the term of this patent is extended or adjusted under 35 U.S.C. 154(b) by 536 days.

(21) Appl. No.: 13/829,509

(22) Filed: Mar. 14, 2013

(65) Prior Publication Data

US 2017/0072154 A1    Mar. 16, 2017

Related U.S. Application Data (60) Provisional application No. 61/690,867, filed on Jul. 6, 2012.

(51) Int. Cl.
| | |
|---|---|
| *A61M 16/04* | (2006.01) |
| *A61M 16/08* | (2006.01) |
| *A61M 16/00* | (2006.01) |

(52) U.S. Cl.
CPC .... *A61M 16/0434* (2013.01); *A61M 16/0404* (2014.02); *A61M 16/0459* (2014.02); *A61M 16/0486* (2014.02); *A61M 16/0816* (2013.01); *A61M 16/0445* (2014.02); *A61M 16/0463* (2013.01); *A61M 16/0488* (2013.01); *A61M 2016/0027* (2013.01); *A61M 2016/0033* (2013.01)

(58) Field of Classification Search
CPC .......... A61M 16/0402; A61M 16/0404; A61M 16/0418; A61M 16/042; A61M 16/0425; A61M 16/0431; A61M 16/0434; A61M 16/0445; A61M 16/0447; A61M 16/0461; A61M 16/0463; A61M 16/0465; A61M 16/0486; A61M 16/0833; A61M 39/105; A61M 39/28; A61M 2210/1032; A61M 2210/1035; A61M 2039/082
See application file for complete search history.

(56) References Cited

U.S. PATENT DOCUMENTS

| | | |
|---|---|---|
| 2,175,726 A | 10/1939 | Gebauer |
| 3,322,126 A | 5/1967 | Rusch et al. |

(Continued)

*Primary Examiner* — Tan-Uyen (Jackie) T Ho
*Assistant Examiner* — Joseph D Boecker
(74) *Attorney, Agent, or Firm* — Riverside Law LLP (57) ABSTRACT

The present invention is a dual lumen endobronchial tube provided with a flexible wall dividing a cylindrical main tube into two lumens, where the outside wall of the main tube is reinforced, preferably by metal wire but alternately by a sufficiently rigid polymer ribbing which will achieve a desired reduction necessary outside wall thickness. The achievement of a reduction in necessary wall thickness enables sufficient hydraulic cross sectional area so that each lumen is capable independently of providing adequate ventilation to a patient even while a ventilation lumen is partly occluded when the insertion end of a bronchoscope or tube is inserted into the adjacent lumen to examine or treat the other lung.

16 Claims, 10 Drawing Sheets

(56) References Cited

U.S. PATENT DOCUMENTS

| | | | | |
|---|---|---|---|---|
| 4,233,984 | A | * | 11/1980 | Walling .............. A61M 16/04 128/207.14 |
| 4,446,864 | A | | 5/1984 | Watson et al. |
| 4,451,252 | A | * | 5/1984 | Martin ............... A61M 5/1582 604/164.11 |
| 4,453,545 | A | | 6/1984 | Inoue |
| 4,819,664 | A | | 4/1989 | Nazari |
| 5,292,305 | A | * | 3/1994 | Boudewijn et al. ............ 604/43 |
| 5,309,906 | A | * | 5/1994 | LaBombard ............ 128/207.14 |
| 5,499,625 | A | | 3/1996 | Frass et al. |
| 5,660,175 | A | | 8/1997 | Dayal |
| 5,795,326 | A | * | 8/1998 | Siman ............................ 604/43 |
| 5,803,080 | A | | 9/1998 | Freitag |
| 5,904,648 | A | | 5/1999 | Arndt et al. |
| 5,954,636 | A | | 9/1999 | Schwartz et al. |
| 6,155,252 | A | * | 12/2000 | Warters .............. A61M 1/0019 128/200.24 |
| 6,443,156 | B1 | | 9/2002 | Niklason et al. |
| 6,454,943 | B1 | * | 9/2002 | Koenhen ................ 210/500.21 |
| 6,513,527 | B1 | | 2/2003 | Abdel-Aziz |
| 6,609,521 | B1 | | 8/2003 | Belani et al. |
| 6,827,710 | B1 | * | 12/2004 | Mooney ............. A61B 17/3417 604/167.06 |
| 7,258,120 | B2 | | 8/2007 | Melker |
| 8,555,887 | B2 | * | 10/2013 | Lisogurski ............... 128/207.15 |
| 2002/0036019 | A1 | * | 3/2002 | Woelfel ................ F16L 11/22 138/115 |
| 2008/0078399 | A1 | * | 4/2008 | O'Neil .............. A61M 16/0443 128/207.14 |
| 2008/0097350 | A1 | * | 4/2008 | Bell ................. A61M 25/0023 604/266 |
| 2011/0265799 | A1 | * | 11/2011 | Lisogurski .......... A61M 16/202 128/207.15 |
| 2012/0017914 | A1 | * | 1/2012 | Watt Lanyau ........... 128/207.14 |
| 2012/0024292 | A1 | * | 2/2012 | Sandmore et al. ...... 128/207.14 |
| 2013/0186407 | A1 | * | 7/2013 | Hammer ................. 128/207.15 |
| 2014/0128672 | A1 | * | 5/2014 | Daher et al. ................. 600/104 |

* cited by examiner

DUAL LUMEN ENDOBRONCHIAL TUBE DEVICE

This application claims the benefit of a provisional application with Ser. No. 61/690,867 filed Jul. 6, 2012, which application is hereby incorporated herein by reference and from which priority is hereby claimed under 35 U.S.C. Sections 119(e) and 120.

FIELD OF THE INVENTION

The present invention relates to devices which provide lung isolation and one lung ventilation, and providing bronchoscope access to one side of the lungs while simultaneously providing respiration flow to the other side of the lung.

BACKGROUND OF THE INVENTION

Endotracheal tubes are used to couple a patient's respiratory system to a breathing apparatus during surgical procedures or emergency situations. A typical endotracheal tube is made of PVC (polyvinyl chloride), silicone, or similar material and has an inflatable cuff positioned a distance centimeters from an end of the tube that is inserted into the trachea. Thus, the tube can be sealed relative to the trachea by inflating the cuff through an inflation line extending along the endotracheal tube. A fitting on an opposite end of the tube couples the endotracheal tube to an artificial respirator or ventilator.

As is also well known to those skilled in the medical arts, a double lumen endotracheal tube is required in many kinds of thoracic, spine, lung or major vascular surgery when it is necessary to perform single lung ventilation or to ventilate both the left and right lungs separately. A conventional double lumen endotracheal tube provides for individualized ventilation of the two lungs with two lumens each having a cuff positioned about a circumference at proximal (tracheal) and distal (bronchial) locations. The bronchial lumen may extend into either the right or left main bronchus while the tracheal lumen remains in the trachea. The prior art double lumen endotracheal tube is limited by its large diameter which can unfortunately lead to bronchial damage and even vocal cord scarring, especially when it is left in place for a long period of time. Thus, when post-operative ventilation support is anticipated for a patient, the double lumen endotracheal tube is usually removed at the end of the operation and is replaced with a conventional single lumen tube. However, the conventional double lumen endotracheal tube can be associated with significant upper airway swelling due to massive fluid resuscitation during the course of a surgical operation. Under these circumstances, replacement of the double lumen endotracheal tube with a single lumen tube in order to attempt to minimize the aforementioned bronchial damage and vocal chord scarring can be a potentially hazardous and occasionally life-threatening procedure. This is due to the fact that it can be very difficult for an anesthesiologist to see the upper airway and vocal chords adequately to replace the single lumen tube in the swollen upper airway.

Further, it is well known that sudden expiration, such as coughs or spasms, during intubation can cause the bronchi to contract as much as 40 percent in diameter, resulting in substantial compression circumferentially about the bronchial cuff. The prior art cuffs respond appropriately for a smooth, blimp-shaped balloon. The mucus covering of the bronchus and the reaction of its muscles are adapted to expel something the size of the bronchial cuff, which is forced upward, sometimes with sufficient force to cause a bronchial lumen to buckle to force the entire tracheal tube upwards. In such circumstances, the bronchial lumen can be moved into a position so that its terminal opening is moved from the desired bronchus to an undesired location in the trachea or even the other bronchus.

The prior art dual lumen tubes have the following disadvantages when used for one-lung respiration combined with a desired bronchoscope examination of either of the two lungs. (a) Insertion and location of cuffs requires a high degree of skill.

(b) Without being able to see the cuff locations after intubation, it is difficult to keep the bronchial lumen tube fixed at a desired position and the tube often enters deep into or comes out of position during anesthesia.

Prior art non-bronchoscopic dual lumen tubes are shown in U.S. Pat. Nos. 4,453,545 and 4,233,984, where the sole intent of the dual lumen structure is to accomplish selective ventilation of the lungs. Neither of these are adaptable to use with a bronchoscope inserted into one of the lumens. The '948 patent device provides a lumen separation which is intended to respond with side to side collapse with a very minor pressure difference. The '545 patent describes that the FIG. 2 device is simply not stable and teaches away from its use in favor of a relatively small diameter bronchial lumen tube with an enlarged cuff. The enlarged cuff lacks position-maintaining tube support which might preserve its location in the lung.

Referring again to surgical environments where dual lumen tube respiration is desired, it is well known that surgery involving the lung or the contents of the thorax often requires cessation of ventilation to one lung to keep the lung immobile while surgery on it is performed or to deflate the lung for better visualization of thoracic structures. Other indications for lung isolation include: containment of unilateral pulmonary bleeding or infection and management of bronchopleural fistula or other pulmonary air leaks. The generally accepted prior art solution for lung isolation is the double lumen endotracheal tube. Modern disposable plastic double lumen tubes are modifications of the original Robert-Shaw tube introduced more than sixty years ago. These endotracheal tubes contain two separate lumens, one for each lung, and ventilation is separated with the use of endotracheal and endobronchial balloon cuffs. The DLT design suffers from two major drawbacks that negatively affect clinical care. The first is the large size of the tube, namely its effective diameter and cross-sectional surface area. Current adult sized double lumen tubes are typically 35-41 French in external circumference; this large size is needed to accommodate the necessary plastic structure (extruded walls) and ventilation passages. Aside from being large, the double lumen tubes are also relatively stiff due to the plastic material used in their construction. The combination of their large and bulky design and undesired stiffness can lead to difficult insertion and even airway injury. Even if insertion is atraumatic, the double lumen tubes' large external diameter increases the pressure on the glottic opening, potentially injuring these delicate structures, especially during prolonged intubations.

The second major design drawback to the prior art double lumen tubes is the relatively small size of the ventilation passages. Even the current prior art double lumen tubes have large external diameters, resulting in a bulky design to house two relatively small diameter channels, thus limiting the size of bronchoscopes, suction catheters, and other instruments that could be inserted into the lungs during use. No adult double lumen tube sizes (35-41 Fr) can accommodate a pulmonary bronchoscope needed to perform diagnostic or therapeutic bronchoscopy (minimum 4.9 mm O.D.). If a diagnostic or therapeutic bronchoscopy exam is to be performed (suction/lavage, bronchial biopsy, bronchial laser) prior to surgical lung resection, a standard large bore endotracheal tube must first be utilized for this part of the procedure to accommodate the large bore bronchoscope. Once the bronchoscopy is completed, the endotracheal tube must be removed and a separate double lumen tube must be inserted in its place, a procedure that is often fraught with risk. A limited lumen diameter imposed on double lumen tubes poses a special clinical challenge when a patient is bleeding from one lung, and lung isolation is warranted. Although a double lumen tube is ideal for lung isolation to prevent flooding the good lung with blood, placement of a double lumen tube severely limits one's ability to perform the diagnostic and therapeutic bronchoscopy necessary to treat this medical emergency.

SUMMARY OF THE INVENTION

The present invention is a dual lumen endotracheal tube provided with a flexible wall dividing a cylindrical main tube into two lumens, where the outside wall of the main tube is reinforced, preferably by metal wire but alternately by a sufficiently rigid polymer ribbing which will achieve a desired reduction necessary outside wall thickness. The achievement of a reduction in necessary wall thickness enables sufficient hydraulic cross sectional area so that each lumen is capable independently of providing adequate ventilation to a patient even while a ventilation lumen is partly occluded when the insertion end of a bronchoscope or tube is inserted into the adjacent lumen to examine or treat the other lung.

The invention dual lumen tube makes critical changes to the standard prior art, such as the 40 cm adult double lumen endotracheal tube, which had the basic configuration of the "Robert-Shaw" classic design. The invention device is composed of two separate lumens, a bronchial and a tracheal, which terminate distally and proximally, respectively. Also present in the invention design are the bronchial and tracheal balloon cuffs, which are utilized to achieve lung isolation. The invention device further comprises, in contrast to the prior art large diameter, thick walled and stiff endotracheal tube, a soft, thin walled material (e.g. plastic, silicone or a similar polymer). The outer wall of this tube is reinforced with an embedded steel coil, wire or polymer ribbing to add structural rigidity to this thin-walled structure. This allows the wall thickness to be reduced, as the tube's rigidity is dependent primarily on the steel coil and not the plastic component. Thinner walls translate to a reduction of the total external diameter of the tube. This construction also allows the invention device tube to be much less rigid, because a reinforced tube can easily flex and bend without compromising the axial rigidity needed to maintain luminal patency. The entire endotracheal tube may in one form comprise a gentle curve as would a standard single lumen endotracheal tube, rather than the multiple curves and angulations of a typical "Robert-Shaw" design tube that can hinder the laryngeal view during laryngoscopy. The combination of 1) smaller size, 2) ergonomic single curve, and 3) more flexible structure can make insertion both easier and less traumatic. Thus, the invention design maximizes the lumen inside diameters while minimizing the total outside diameter of the main tube, whereby only two adult sizes may be needed to satisfy a wide range of patient variability. Thus, rather than having size 35F, 37F, 39F, and 41F, the invention design may be supplied "small adult" and "large adult" sizes. There are benefits mentioned in the provisional that may need to be included here such as: cost savings to medical facilities to fewer inventory devices, simplification of procedure and less chance for an error by the practitioner in having only 2 sizes that are adequate for left and right lung ventilation, etc.

Further, current prior art dual lumen endotracheal tube designs require separate "right sided" and "left sided" configurations depending on whether the bronchial portion of the tube is to be placed in the right or left mainstem bronchus. The invention tube, is preferably provided in one configuration. A user vertically rotates the invention device 180 degrees to change the orientation of the bronchial lumen from left to right. To use the invention device as a left sided dual lumen endotracheal tube designs, a user inserts the tube with the bronchial lumen pointing to the patient's left, thus placing the bronchial lumen into the left mainstem bronchus. To use the invention device as a right sided dual lumen endotracheal tube designs, a user will reverse the just described rotation.

To aid in correct insertion of the invention dual lumen endotracheal tube designs, the invention may be used with a specialized stylet to create the proper tube orientation and curvature. The stylet is semi-rigid and malleable to aid in tube insertion into the airway, but the stylet distal tip will be more flexible. This design will allow the stylet to point the bronchial lumen tube in the right direction (to a mainstem bronchus of one's choosing) without posing an increased risk of airway rupture or serious injury.

In another form it will be steerable and will integrate a video chip camera to enable visualization of the airway. This will enable the practitioner to obtain and maintain proper device positioning within the airway.

In another form of the invention, the tracheal and/or bronchial balloon cuffs are changed from the typical smooth blimp shaped cuffs currently in use. The cuffs will change in: 1) shape and/or 2) surface texture. Rather than being blimp shaped, the balloon cuffs would retain a more precise cylindrical configuration similar to the surface area in contact with the airway would be maximized. Their texture, rather than being smooth and slippery, may be roughened such that a small amount of friction is formed between the cuff and airway. These two attributes are likely to maximize the air seal for ventilation, while minimizing the balloon pressure needed to achieve this seal. Furthermore, the increased friction would reduce the likelihood of tube dislodgement or movement during clinical use.

The main tube of the invention device is a reinforced flexible plastic tube and contains a flexible internal membrane throughout its entire length that divides the space into two separate lumens. Unlike the current dual lumen endotracheal tube designs, the separation between the lumens is not achieved by a thick rigid internal wall, but rather by a flexible intraluminal membrane. In cross-section, the membrane configuration is semi-lunar, with the convex curve facing the tracheal lumen. The attachment points of this membrane to the inner wall of the tube are slightly offset away form the midline in the direction of the bronchial lumen, so that the cross-sectional areas of the two lumens are relatively balanced. During both two and one-lung ventilation, this membrane rests in its neutral position. However, the flexible nature of this divider-membrane allows it to deform in order to accommodate larger bronchoscopes. Thus, should a large bronchoscope need to be inserted into the invention device, it would preferably be introduced into the tracheal lumen. The intraluminal membrane would then deform away from the bronchoscope, creating a larger lumen that can accommodate this large instrument. The invention device may be pulled back so that its distal bronchial tube tip is above the carina if a full (two lung) bronchoscopy exam is to be performed. This flexible intraluminal membrane design also allows for other large caliber tubes to be inserted, such as large bore suction catheters.

For the one form of operation of the invention device, a bronchial lumen connector tube connects to the bronchial lumen through a side-orifice in the main tube. This connector slides over the tube external diameter via a ring, and the tubular orifice of the connector lines up with the side-orifice of the bronchial lumen, where it is permanently bonded. A specialized Y-piece may be connected to the two connectors. This Y-piece serves the usual dual function of 1) allowing for simultaneous ventilation of both lumens with one ventilator, and 2) allowing for bronchoscopy to be performed during positive pressure ventilation. However, this Y-piece will have one unique feature not seen in current Y-piece design, namely it will contain built in flow control clamps. Thus, rather than having to attach a metal instrument clamp to close one tube during one-lung ventilation (as is often performed), a Y-piece clamp is simply closed. One-lung ventilation can now be performed while still leaving the Y-piece in the circuit, without the need for an external instrument clamp.

It is also an object of the invention to incorporate adjustable gas flow clamps onto the Y connector tubes with an external attachable gas flow sensor to monitor gas flow.

It is also an object of the invention to incorporate tube occluding clamps onto the Y connector tubes to occlude one tube at a time if desired.

DETAILED DESCRIPTION OF THE INVENTION

The invention is now discussed with reference to the figures.

Figure 1:
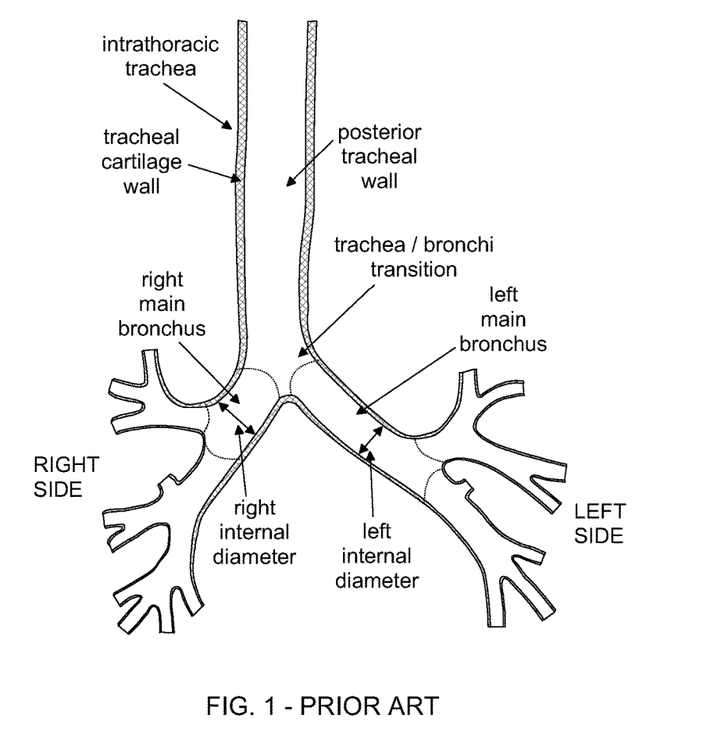
FIG. 1 is a front, cross section view of a human lung, shown the tracheal and bronchial structures relevant to the present invention.

FIG. 1 is a front, cross section view of a human lung, shown the tracheal and bronchial structures relevant to the present invention. Especially relevant are the relative locations of the main bronchi to the trachea.

Figures 2, 3:
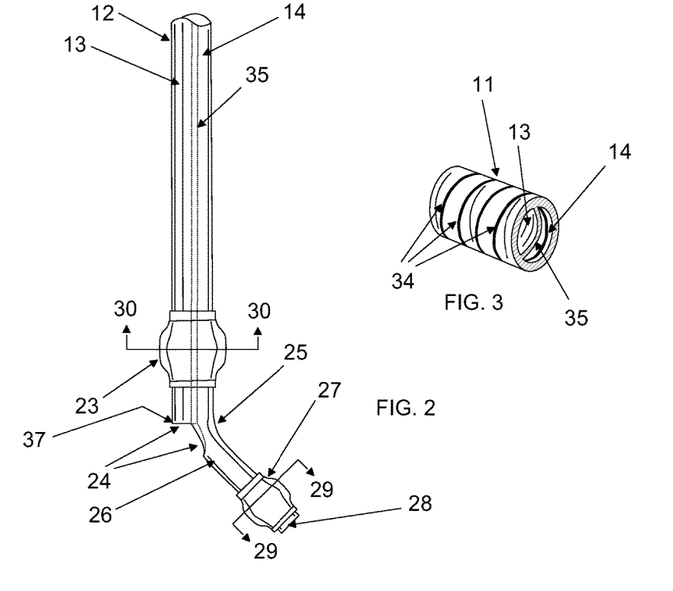
FIG. 2 is a front view of one form of the invention dual lumen tube.
FIG. 3 is a perspective of a section of a dual lumen portion of the invention dual lumen tube showing wire reinforcement thereof.
Figure 4:
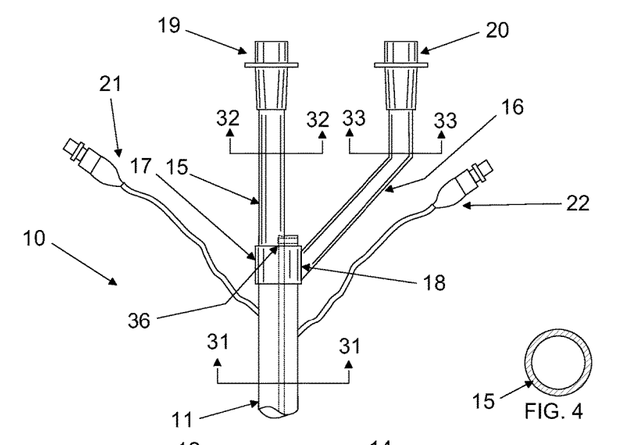
FIG. 4 is section 32 of FIG. 2.
Figure 5:
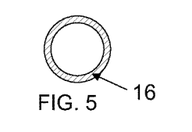
FIG. 5 is section 33 of FIG. 2.

FIG. 2 is a front view of one form of the invention dual lumen tube 10, having a proximal tube section 11 and a distal tube section, which are continuous and joined to each other but are shown with an indeterminate length break appropriate to an overall length of tube 10. For example an overall length of tube 10 for an adult will typically be about 40 centimeters. Overall length of tube 10 is reduced appropriately for pediatric and small adult sizes. It is critical to the objects of this invention that the outside diameter of sections 11 and 12 be less than or equal to approximately 13 millimeters for a large adult size and less than or equal to approximately 12 millimeters or less for a small adult size. It is a further critical feature of this invention to provide an outside wire-reinforced wall thickness for sections 11 and 12 at less than or equal to approximately 2.5 millimeters, and preferably less than or equal to approximately 1.5 millimeters, where a flexible wall separating two internal lumens has a wall thickness of less than or equal to approximately 2.5 millimeters, preferably less than or equal to approximately 1.5 millimeters, and most preferably from approximately 0.5 to 1.5 millimeters. It is further preferred that hydraulic cross section areas of two internal lumens in sections 11 and 12 are about equal before insertion of any solid device into either lumen. These restrictions on dimensions establish hydraulic cross sections within both lumens of sections 11 and 12 which are adapted to accomplish the objects of the invention, i.e. that full and required ventilation and respiration for a patient can be achieved by ventilation of one lung while the other lung is isolated for examination or treatment as described herein. The present inventors have thereby minimized outside wall thickness by helical wire reinforcement 34, as shown in FIG. 3, engaged to the polymer of the outside wall, which extends internally from sealing lines 38 and 39 to form lumen divider wall 35 between lumens 13 and 14. Referring again to FIG. 2, it is preferred that wire reinforcement shown in FIG. 3 extend the lengths of sections 11 and 12, from point 36 to point 37.

Figure 6:
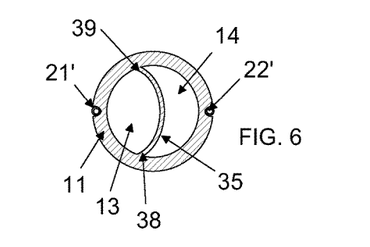
FIG. 6 is section 31 of FIG. 2.
Figure 7:
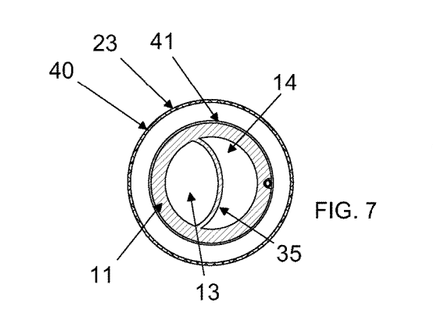
FIG. 7 is section 30 of FIG. 2.
Figure 8:
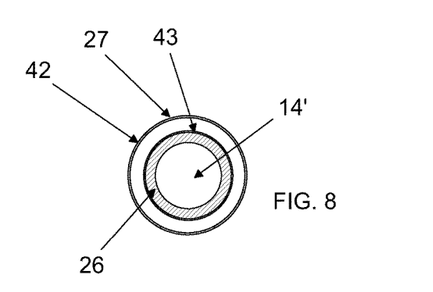
FIG. 8 is section 29 of FIG. 2.

FIG. 2 shows that section 11 extends up to transition piece 18, wherethrough one lumen is extended up to single conduit 15 and 15 mm universal ventilator connector 19 and where the other lumen is extended sideways to single conduit 16 and 15 mm ventilator connector 20. Connectors 19 and 20 are adapted to either receive a ventilator connection or to receive an insertable object, such as a bronchoscope, a vacuum tube or a positioning stylet. FIG. 6 shows additional detail of a cross section of section 11 (which is identical with most of the length of section 12), where wall 35 is formed so that it is convex to lumen 14 and concave to lumen 13. Sealing lines 38 and 39 are located to the left of a cylindrical center line. Cuff inflation tubes 21' and 22' correspond to, referring again to FIG. 2, cuff inflation valves and tubing ends 21 and 22, where, respectively, those ends 21 and 22 are operated to inflate or deflate tracheal cuff 23 and bronchial cuff 27. As such, inflated cuff 23 is shown in FIG. 7 as section 30 of FIG. 2, where an outside layer 40 is sealed to an inside layer 41, forming a maximum outside diameter of about 30 millimeters for an adult trachea and inflated cuff 27 is shown in FIG. 8 as section 27 of FIG. 2, where an outside layer 42 is sealed to an inside layer 43, forming a maximum outside diameter of about 22 millimeters for an adult bronchus.

Figure 9:
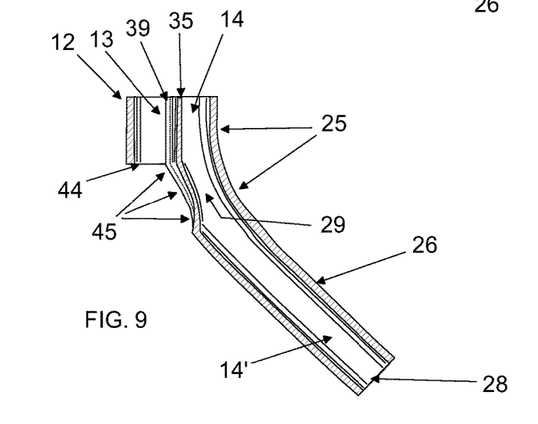
FIG. 9 is an enlarged, cutaway section of a distal end of the invention dual lumen tube of the invention dual lumen tube of FIG. 2.
Figure 10:
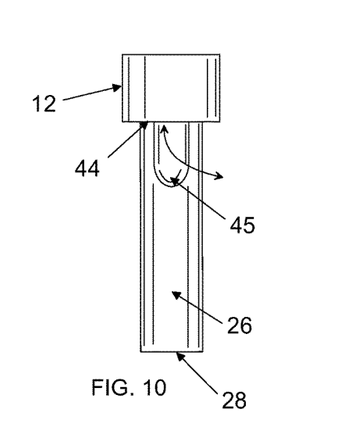
FIG. 10 is a left side view of the distal end of the invention dual lumen tube of FIG. 2.

Referring to both FIGS. 2 and 9 for a description of a distal end of tube 10, section 12 terminates at point 37, with lumen 13 having a distal opening 24, which comprises a horizontal part 44 and an angled, concave part 45. It is another important feature of the invention that the combination of airflow parts 44 and 45 allow for ventilation of a lung even if substantial portions of opening 24 are occluded by tissue or fluid. Angled bronchial extension 26 shall be formed to have an axis in its lumen extension space 14' about 20-40 degrees from an axis of section 12, so that it is more easily located in a desired bronchus at insertion. FIG. 10 provides a clearer view of the part 45. A transition section 25 between section 12 and a straight part of bronchial tube 26 may be formed separately from section 12 and bonded and sealed to an appropriate lumen opening of section 12 to achieve a desired angle orientation.

Figure 11:
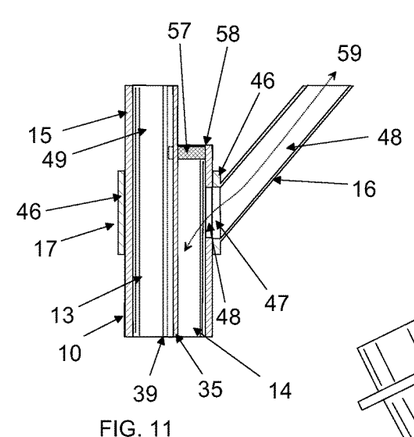
FIG. 11 is an enlarged, cutaway section of a proximal end of the invention dual lumen tube of FIG. 2.

FIG. 11 is an enlarged, cutaway section of portion of a proximal end of the invention dual lumen tube of FIG. 2, where lumen 13 extends upward to lumen extension 49 defined by the inside walls of single conduit 15. Transition piece 17 comprises a circumferential band wall 46 defining circular opening 47, the opening 47 having a diameter of about 8 millimeters or more to accommodate insertion of a bronchoscope, tubing or stylet. A similarly sized circular opening 48 is formed in section 11 and is aligned with opening 47. A sealing plug 57 seals an upper, terminal end of lumen 14 at opening 58.

Figure 12:
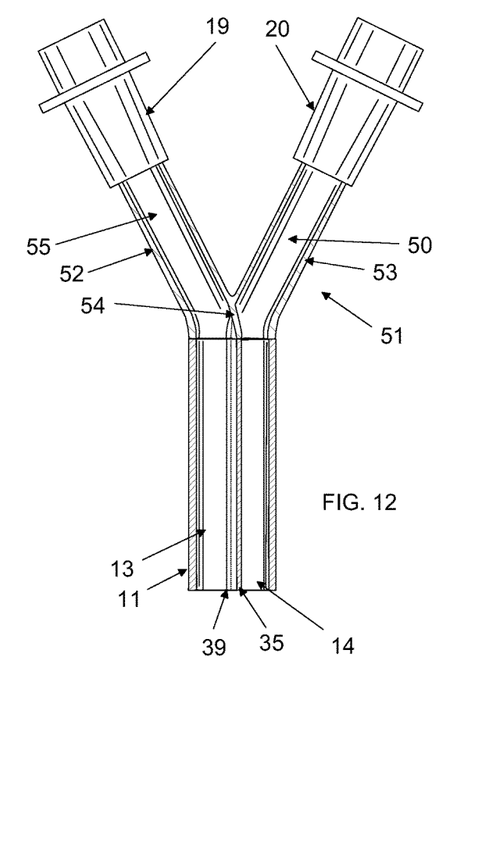
FIG. 12 is an enlarged, cutaway section of an alternate proximal end of the invention dual lumen tube of FIG. 2.

FIG. 12 is an enlarged, cutaway section of an alternate proximal end of the invention dual lumen tube of FIG. 2, where a Y-section 51 comprises single conduits 52 and 53 respectively extending in spaces 55 and 56 the spaces of lumens 13 and 14. Short flange 54 maintains a gas tight separation of spaces 55 and 56, as does wall 35 maintain a gas tight separation of lumens 13 and 14.

Figures 13, 13A:
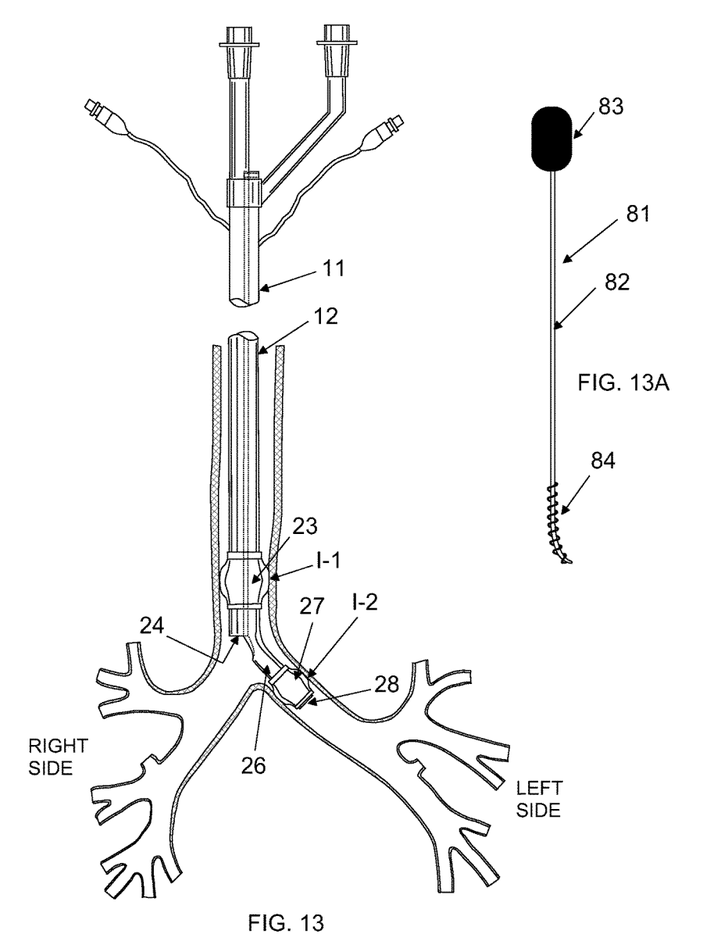
FIG. 13 is the invention dual lumen tube of FIG. 2 shown placed for left bronchus placement of the bronchial tube as in the lungs shown in FIG. 1.
FIG. 13A is a side view of an end-adjustable stylus adapted to direct precise placement of a bronchial tube at the distal end of the invention dual lumen tube.

FIG. 13 is the invention dual lumen tube of FIG. 2 is shown placed for left bronchus placement of the bronchial tube 26 as in the lungs shown in FIG. 1, where interface I-1 defines an interface between sealingly inflated cuff 23 and the tracheal walls and interface I-2 defines an interface between sealingly inflated cuff 27 and the left bronchus. FIG. 13A shows an end-adjustable stylet 81 comprising a slender shaft 82 terminating in an adjustable end 84, which is adjustable toward the right in the drawing by depressing a button on handle 83. The stylet 81 is capable of being inserted into single conduit 16 and then through lumen 14 to engage bronchial tube 26 for placement into a bronchus as shown in FIG. 13.

Figure 14:
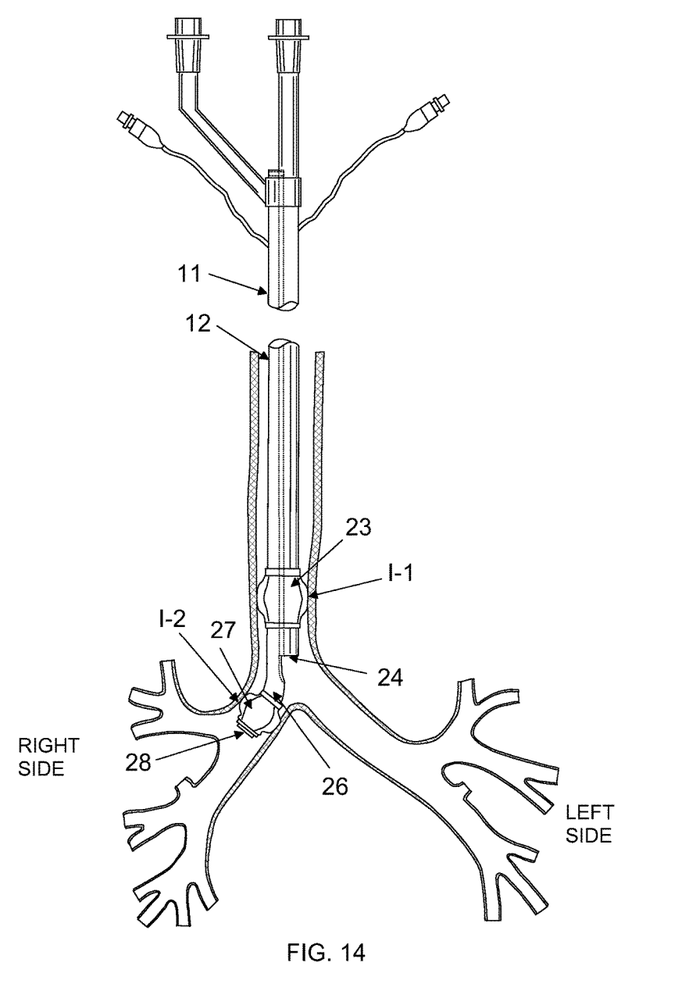
FIG. 14 is the invention dual lumen tube of FIG. 2 shown placed for right bronchus placement of the bronchial tube as in the lungs shown in FIG. 1.

FIG. 14 is the invention dual lumen tube of FIG. 2 shown placed for right bronchus placement of the bronchial tube 26 as in the lungs shown in FIG. 1, where interface I-1 defines an interface between sealingly inflated cuff 23 and the tracheal walls and interface I-2 defines an interface between sealingly inflated cuff 27 and the right bronchus.

Figure 15:
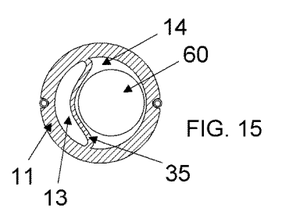
FIG. 15 is cross section 31 of FIG. 2 showing a cross section of a bronchoscope or other slender cylindrical element within one lumen, leaving the adjacent lumen available for ventilation.

FIG. 15 is cross section 31 of FIG. 2 showing a cross section of a bronchoscope or other slender cylindrical element 60 within one lumen 14, leaving the adjacent lumen 13 available for ventilation.

Figure 16:
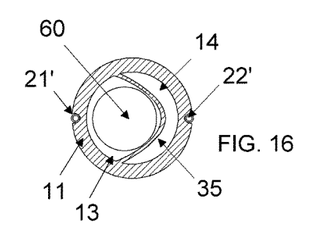
FIG. 16 is cross section 31 of FIG. 2 showing a cross section of a bronchoscope or other slender cylindrical element within one lumen, leaving the adjacent lumen available for ventilation.

FIG. 16 is cross section 31 of FIG. 2 showing a cross section of a bronchoscope or other slender cylindrical element 60 within one lumen 13, leaving the adjacent lumen 14 available for ventilation.

Figure 17:
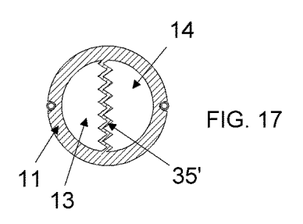
FIGS. 17 and 18 are cross section 31 of FIG. 2 showing alternate forms of a flexible wall separating the lumens.
Figure 18:
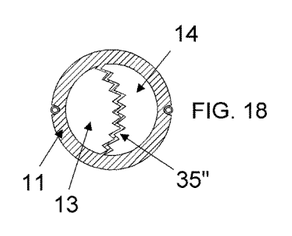

FIGS. 17 and 18 are cross section 31 of FIG. 2 showing alternate accordion forms 35' and 35" of a flexible wall separating the lumens.

Figure 19:
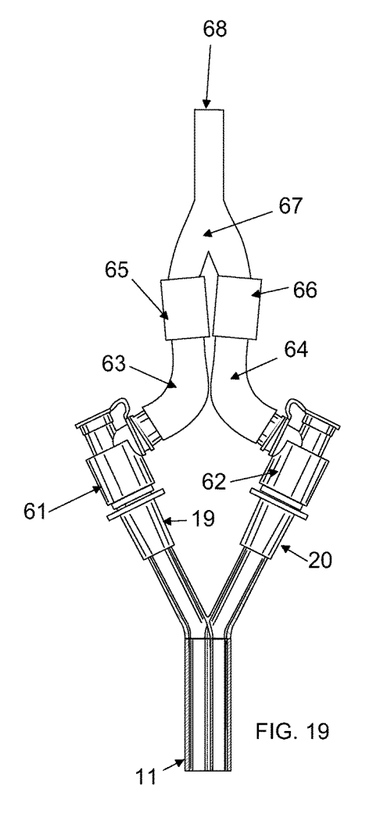
FIG. 19 is the alternate proximal end of FIG. 12, where each proximal terminal end of each lumen is connected with a separate ventilation tube, where separate ventilation tubes are joined into a single ventilation tube and each separate ventilation tube is optionally circumferentially enclosed with a control or monitor element.
Figure 20:
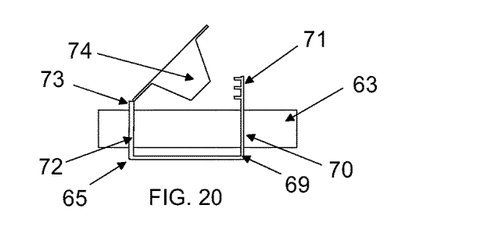
FIG. 20 is one form of a control element for a separate ventilation tube of FIG. 19, where a pivoting clamp is shown in an open position.
Figure 21:
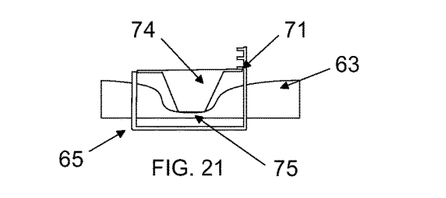
FIG. 21 is one form of a control element for a separate ventilation tube of FIG. 19, where a pivoting clamp is shown in an closed position.

FIG. 19 is the alternate proximal end of FIG. 12, where connectors 19 and 20 are respectively connected to separate ventilation tubes 63 and 64 at connectors 61 and 62. Tubes 63 and 64 extend to join at junction 67. Along the lengths of tubes 63 and 64 are optionally positioned one or more of circumferentially encasing a control or monitor elements 65 or 66. Elements 65 or 66 may be electrical or pneumatic measurement sensors whose output can be recorded to an electrical recording device for pressure and volume of ventilation to each of tubes 63 and 64. Elements 65 or 66 may also be flow controllers as in FIG. 20 is one form of a control element 65 for a separate ventilation tube 63, where a pivoting clamp 65 is shown in an open position. Clamp 65 is a well known tube clamping device that comprises a frame 69 with a horizontal plate connecting two vertical plates 70 and 72, each defining an opening for tube 63 therethrough. An occluding bar 74 is fixed by living hinge to a top end of plate 72, so that it rotates downward to a closed position, as shown in FIG. 21, where tube 63 is shut tight with a free end of bar 74 engaged to lateral extensions of plate 70. Additional lateral extensions are available on plate 70 to provide for partial closing of tube 63.

The assembly of FIG. 19 allows for independently variable ventilation of each lung in combination with the tube 10 of FIG. 2.

Figure 22:
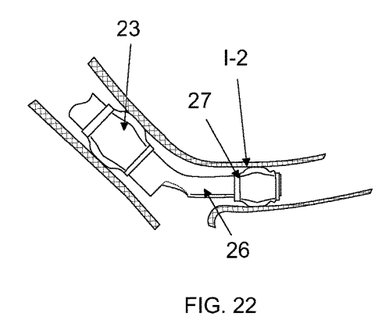
FIG. 22 is a broken away view of the bronchial tube within the left bronchus as in FIG. 13, angled to illustrate cuff and organ wall contact.

FIG. 22 is a broken away view of the bronchial tube within the left bronchus as in FIG. 13, angled to illustrate cuff and organ wall contact.

Figure 23:
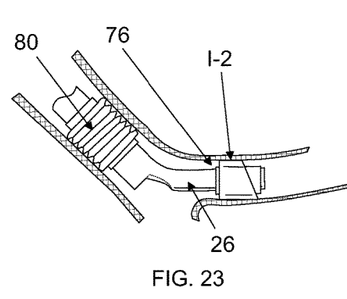
FIG. 23 is the view of FIG. 22 with an alternate tracheal and bronchial cuff.

FIG. 23 is the view of FIG. 22 with an alternate tracheal cuff 80 with a roughened, textured or undulating surface for improved engagement to the tracheal wall. Bronchial cuff 76 is shown with a proximal end flattened and a distal end angled to improve engagement to the tracheal wall.

Figure 24:
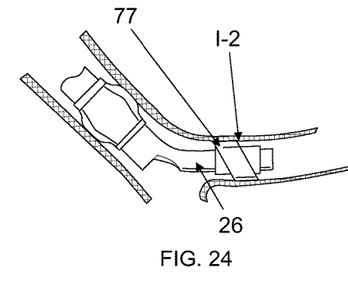
FIG. 24 is the view of FIG. 22 with an alternate bronchial cuff.

FIG. 24 is the view of FIG. 22 with an alternate bronchial cuff 77 is shown with a proximal end angled and a distal end angled in the same direction to improve engagement to the tracheal wall.

Figure 25:
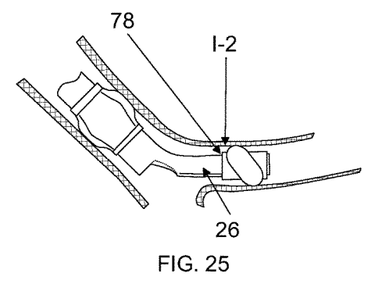
FIG. 25 is the view of FIG. 22 with an alternate bronchial cuff.

FIG. 25 is the view of FIG. 22 with an alternate bronchial cuff 78 is shown with a proximal end flattened and a distal end angled to improve engagement to the tracheal wall.

Figure 26:
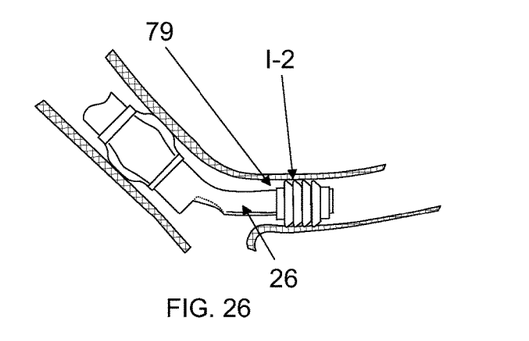
FIG. 26 is the view of FIG. 22 with an alternate bronchial cuff.

FIG. 26 is the view of FIG. 22 with an alternate bronchial cuff 79 is shown with a wall contact surface adapted so that a distal part of set of adjacent engaging rings have a different surface angle relative to tube 26 than a distal part, imparting an easier insertion than withdrawal when in contact with the bronchus.

In a further form of invention reinforcement of the sections 11 and 12 of FIG. 2, helical reinforcement may be by way of extrusion molding of a flexible polymer such as PVC, silicone or a polymer of similar specifications in combination with a narrow gauge stainless steel or metal wire or a rigid polymer ribbing (well known for plastic reinforced hose and tubing, such as integral PVC ribbing) with helical spacing of from 1 millimeter to 10 millimeters. Alternately, but less preferably, sections 11 and 12 of FIG. 2 may be reinforced with a mesh or web of polyester yarn or graphite fibers to further reduce outside wall thickness. Still alternately, the helical reinforcing may be replaced with spaced apart ribs or rings of the same materials as stated for helical reinforcement.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

We claim:

1. An endotracheal tube with a main tracheal tube that defines a longitudinal cylindrical internal space that is divided lengthwise by a dividing wall to define two internal and adjacent tracheal lumens within the main tracheal tube, the endotracheal tube being adapted for a tracheal cuff sealing by way of a tracheal cuff of a patient's trachea, the tracheal cuff being supported from the main tracheal tube and being further adapted for a bronchial cuff sealing by way of a bronchial cuff of a bronchus of the patient, the bronchial cuff being supported from a bronchial tube that extends downward from the main tracheal tube and which defines an internal bronchial tube lumen extending one of the tracheal lumens comprising:
  a) the dividing wall forms two sealing attachment lines lengthwise down an inside surface of the main tracheal tube, whereby the two sealing attachment lines are offset from a midline of the tracheal tube such that the dividing wall extends away from the inside surface at points that are offset from the midline of the tracheal tube, wherein the cross section areas of the two internal and adjacent tracheal lumens are about equal when the dividing wall is at rest;
  b) at a lower end of the main tracheal tube, the tracheal cuff is located above a first opening of the main tracheal tube defined at a distal end of the tracheal lumen that does not extend to the bronchial tube lumen; and
  c) the bronchial tube lumen terminates at a distal bronchial opening and the bronchial cuff is located above the distal bronchial opening.

2. The endotracheal tube of claim 1 wherein the thickness of the dividing wall is from 2.5 to 0.5 millimeters.

3. The tube of claim 1 wherein the dividing wall is smooth and semilunar at rest.

4. The endotracheal tube of claim 1 wherein the dividing wall is segmented in an accordion shape but is generally in a flattened orientation.

5. The endotracheal tube of claim 1 wherein the dividing wall is segmented in an accordion shape but is generally in a semilunar orientation.

6. A specialty endotracheal tube comprising:
  a) a tracheal tube and a bronchial tube, the bronchial tube extending from a distal end of the tracheal tube;
  b) a tracheal tube lumen defined by inside walls of the tracheal tube;
  c) a dividing wall longitudinally dividing the tracheal tube lumen and, with the inside walls of the tracheal tube, defines a short lumen and a long lumen adjacent to each other in the tracheal tube;
  d) the short lumen comprising a first upper opening and a first lower opening near a connection of the bronchial tube to the distal end of the tracheal tube;
  e) the long lumen comprising a second upper opening and a second lower opening into a bronchial lumen defined by inside walls of the bronchial tube;
  f) the bronchial tube lumen comprising a third lower opening;
  g) a first inflatable cuff fixed above the first lower opening of the short lumen on an outside wall of the tracheal tube;
  h) a second inflatable cuff fixed above the third lower opening of the bronchial lumen on an outside surface of the bronchial tube; and
  i) two sealing attachments of the dividing wall along the inside walls of the tracheal tube are offset from a midline of the tracheal tube such that the dividing wall extends away from the inside walls at points that are offset from the midline of the tracheal tube, defining cross sectional areas of the short lumen and long lumen that are about equal when the dividing wall is at rest.

7. The specialty endotracheal tube of claim 6 wherein the dividing wall is semilunar in cross section shape at rest.

8. The specialty endotracheal tube of claim 6 wherein the dividing wall comprises, in cross section, a convex surface opposite an inside wall of the tracheal tube of the long lumen.

9. The specialty endotracheal tube of claim 8 wherein the dividing wall is flexible such that insertion of a medical device into the long lumen, due to an offset sealing attachment of the dividing wall, prevents the short lumen from becoming occluded for ventilation of a patient.

10. The specialty endotracheal tube of claim 6 wherein the dividing wall comprises, in cross section, a concave surface opposite an inside wall of the tracheal tube of the short lumen.

11. The specialty endotracheal tube of claim 10 wherein the dividing wall is flexible such that insertion of a medical device into the short lumen, due to an offset sealing attachment of the dividing wall, prevents the long lumen from becoming occluded for ventilation of a patient.

12. The specialty endotracheal tube of claim 6 wherein the dividing wall comprises, in cross section, a convex surface opposite an inside wall of the tracheal tube of the short lumen.

13. The specialty endotracheal tube of claim 12 wherein the dividing wall is flexible such that insertion of a medical device into the long lumen, due to an offset sealing attachment of the dividing wall, prevents the long lumen from becoming occluded for ventilation of a patient.

14. The specialty endotracheal tube of claim 13 wherein the dividing wall comprises, in cross section, a concave surface opposite an inside wall of the tracheal tube of the long lumen.

15. The specialty endotracheal tube of claim 6 wherein an inside diameter of the tracheal tube is 10 millimeters and an outside diameter is 13 millimeters.

16. An endotracheal tube comprising:
- a tube having an inner wall and a membrane attached to the inner wall defining a first lumen and a second lumen within the tube, wherein the membrane extends away from the inner wall at points that are offset from a midline of the tube;
- wherein, when the membrane is at rest, the cross sectional areas of the first and second lumens are about equal, and
- wherein, when an instrument is inserted into the first lumen, the membrane is suitably flexible to increase the cross sectional area of the first lumen while maintaining in the second lumen a reduced cross sectional area suitable for ventilation through the second lumen.

* * * * *